US00PP09814P

United States Patent [19]

Zaandam

[11] Patent Number: Plant 9,814

[45] Date of Patent: Mar. 4, 1997

[54] IXORA PLANT—'DIORA'

[76] Inventor: Diana Zaandam, 340 Catalonia Ave., Coral Gables, Fla. 33134

[21] Appl. No.: 551,487

[22] Filed: Nov. 1, 1995

[51] Int. Cl.[6] ..... A01H 5/00

[52] U.S. Cl. ..... Plt./54.1

[58] Field of Search ..... Plt./54.1

[56] References Cited

U.S. PATENT DOCUMENTS

P.P. 9,200 7/1995 Pitman ..... Plt./54.1

*Primary Examiner*—James R. Feyrer
*Attorney, Agent, or Firm*—Reginald A. Richardson

[57] ABSTRACT

A new and distinct variety of *Ixora chinensis* plant denominated 'Diora', which is of the Dwarf Hybrida Ixora class, and which is characterized particularly by its milk white flowers, its large inflorescence and copious number of flowers and buds per large corymb. This plant has an especially dwarf habit, heavy branching and forms a short and uncommonly compact shrub with a very dense canopy of uniform, dark green leaves.

1 Drawing Sheet

BACKGROUND OF THE INVENTION

The present invention relates to a new and distinct variety of hybrid Ixora plant. The plant of this invention is dwarf, very compact, well branched and presents repeated corymbs of numerous white blossoms nearly continuously under proper care. Like other members of the species, this plant is a tropical evergreen which presents repeated corymbs of large numbers of white flowers of startling beauty and attractiveness; thus, with the compact stature characteristic of this plant, offers use as a potted flowering specimen. The fragrance of the flowers of this plant is not distinctive. Specimens of this plant can be cultured in plant containers for culture in temperate climates as a house plant, or, the plant is an attractive appointment to the landscape as a specimen plant, can be used as border plants in foundation plantings; and presents a nearly continuous splash of color in garden settings in gardens in frost free areas.

The plant was discovered as a spontaneous seedling in a nursery area in Latour, Suriname, South America, in an area where numerous varieties of hybrid ornamental Ixora plants were being produced for retail sales. Because this plant was unusual in its compactness, it was immediately isolated for further observation. This plant was taken from an area where several species of Ixora were being cultured, and the characteristics of this plant do not conform to those of varieties being grown in the nursery, it is suspected that this plant is cross-species in genetic background. This plant was observed in culture and allowed to mature into a blooming specimen. Upon observation of the highly desirable and attractive blooming and growth habit of this plant, I directed the asexual propagation of the plant by the taking and rooting of terminal cuttings at the nursery location. The specimens so cultured proved to be identical to the originally selected seedling in every distinguishing characteristic.

SUMMARY OF THE INVENTION

The plant of this application, 'Diora' is a highly attractive, dwarf Ixora plant of unknown, but suspected *I. chinensis* species. It forms small specimens of bushy, upright habit, with plural stems. This plant branches prolifically and has very short internodes to form specimens of very extreme compactness. Under proper conditions of culture and feeding this plant will bloom nearly continuously; presenting numerous corymbs of highly dense flowers of nearly pure white coloration. Corymbs appear nestled into the surface of the bush formed and are in stark and attractive contrast to the moderate to deep green, thick foliage. Leaves are thick and healthy in appearance and leathery in thickness. This plant responds well to pruning to encourage more densely branched specimens and stouter, thicker specimens. Due to its very dwarf stature, this plant may be cultured in plant containers and seasonally brought indoors to be protected against the cold; that its territory of culture can be greatly expanded in this manner by culture as a house plant. Under optimum conditions this plant begins prolifically flowering as a very small specimen. The very precocious nature of this plant is one of the most desireable and valuable attributes of this plant which sets it apart from other commercially available varieties of Ixora. Flowers are copious in numbers, small, milky white in color and have no noticeable distinctive fragrance.

BRIEF DESCRIPTION OF THE VIEWS OF THE DRAWING

The plant of this application is depicted in the drawing in full color in the accompanying photographs, in which.

Figure 2:
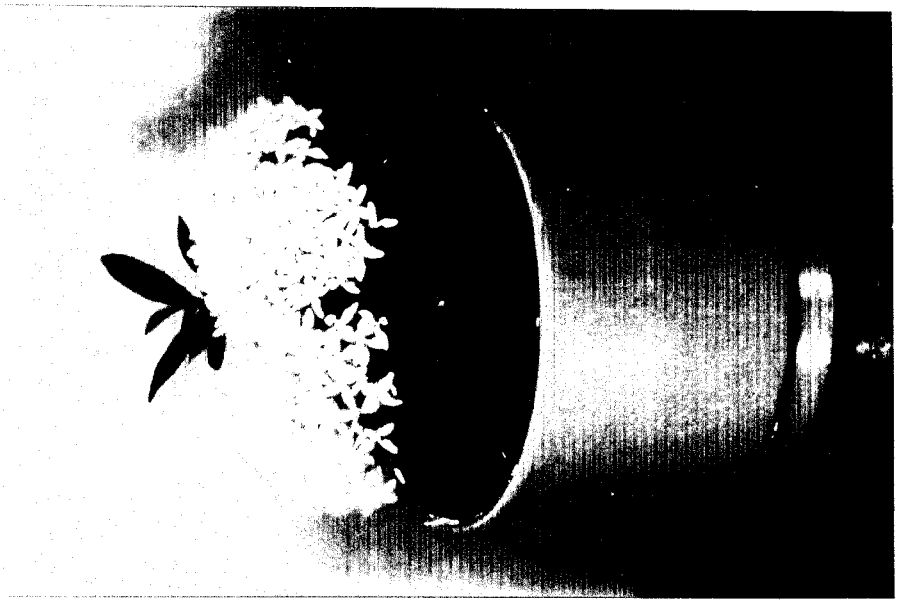
FIG. 2 depicts, in closer view, a young specimen of the plant with two corymbs in fully opened flowering stage. This photograph illustrates the unusual precocity of 'Diora', which tends to flower heavily even on liner sized specimens.

The botanical descriptions to follow are taken from specimens cultured under nursery conditions typical within the industry under commercial conditions. While the phenotype of this plant might be expected to show some variability in culture under differing cultural conditions, the specifications of characteristics to follow are believed to be true to the plant, and may be relied on to help identify the plant of this disclosure. All color values to follow were taken from the color references noted in the *Exotica Horticultural Color Guide*, except where terms of ordinary meaning are employed. It is to be understood that, while the genotype of this plant has been established to be stable, the color expressions and phenotype of this plant may vary widely based on the cultural practices, such as fertilization program and the level of light and temperature under which this plant is grown.

BOTANICAL DESCRIPTION OF THE PLANT

Origin: Spontaneous seedling of unknown origin. Discovered in a location where several Ixora species had been under culture.

Classification:

*Botanical.*—Hybrid, believed to be a member of *Ixora chinensis*; species undetermined with certainty, and possibly an interspecific hybrid.

*Commercial.*—Evergreen flowering tropical shrub.

Asexual propagation: Most efficiently multiplied by taking of cuttings having 4 nodes, and rooting under conventional optimum rooting conditions.

Habit: Dwarf shrub. Multiple main stems; moderate to heavy branching. Tolerates temperatures to freezing; optimum growth and flowering in temperatures of 60 degrees F. or higher. Normally grows to about 30 to 40 cm, as determined by pruning. Normally taller than wide. Hardy under tropical conditions.

Growth: Moderately to weakly vigorous. A typical rooted cutting, when planted in a 20 cm pot will reach a mature size in approximately 18 months and will attain a height of about 30 to 40 cm and a breadth of approximately 20 to 25 cm.

Canopy: Very dense, compact, due to short internodes, multiple stems and branching.

Bark: Newly formed bark is green and matt, similar color to the foliage. Older bark is brown and takes on a russetted appearance.

Internodes: Internodes typically measure 1.5 cm. or less. Internode length tends to increase with short days or in culture under less than full sunlight. An overabundance of nitrogen fertilizer can cause an increase in the length of the internodes.

Foliage: The shape of the leaves is generally oblanceolate/elliptic with acuminate tips and bases. Arrangement is opposite, leaf pairs are generally alternate. Stipules are absent. Petioles are short and generally measure no more than 2.5 mm in length and about 1.5 mm in width. Petioles are darkened with anthocyanin coloration at the swollen attachments to the nodes. The upper surface of newly formed tender leaves is near (76). Mature leaves are darker and greener than, but closest to (70) in color. The lower surface of newly formed leaves is distinctly lighter than top surfaces and contrasts therewith; typically the colors will be between (71) and (76), the undersurfaces darken with age and maturity of the leaves. Margins are entire. The top surfaces of leaves are smooth and semi-glossy and the bottom surfaces are matt. Leaf midribs are near (73) in color and lighter than the top surface coloration of the leaves in all stages of maturity. The midribs protrude slightly from the bottom surface of the leaves, and are slightly darker in coloration compared to surrounding tissue, but do not form a noticeable indentation to the touch on the top surface of the leaf lamina. Mature leaf blades are symmetrical and generally uniform in size; and, normally measure about 3–7 cm in length and 1–1.3 cm in width.

Figure 1:
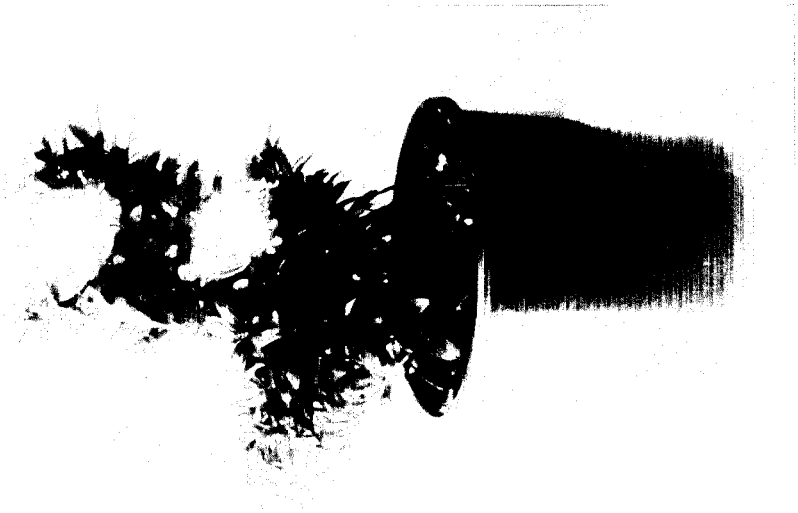
FIG. 1 shows a mature market size plant in a 20 cm container. This specimen depicts the multiple main stems of the plant and generally shows the branching character of the plant. Leaf uniformity, leaf arrangement and leaf and bark color and textures are also shown. Corymbs of varying stages of maturity are shown in the characteristic density of buds and flowers, with the character and color of flowers shown in natural tones.

Inflorescence: Flowers are borne in copious quantities in crowded corymbs which range in diameter from about 6 to 8 cm. Corymb development is progressive and continuous on an actively growing specimen when cultured under optimum growing conditions. A mature specimen of this plant may present as many as 9, or more corymbs forming at any given time as depicted in FIG. 1. Corymb buds arise out of axils of leaves near the terminals of stems, with about one per terminal per stem at some stage of development at any given point. Corymbs are composed of compact clusters of individual small flowers, of milk white color, which together are globose in shape, more cauldiflorous than flat. Individual flower count per corymb will vary between about 53 to 105 flowers. Some flowers show a thin, pink margin, near (38) in color. The corolla of each flower is tubular, and comprises 4 terminal lobes, or petals, which are jointed at the juncture to the corolla by a narrow claw which is more elongated in mature flowers and shorter in freshly opened flowers. It has been noted that between 5 and 10% of the flowers will have 5 petals and 5 stamens. Petals are milk white in color, near (1–) and have a length of between 8 to 9 mm and a width of between 3–4 mm. Margins are complete, may be generally flat or involuted. Corolla tubes are green at the base and progressively fade to near milk-white at the junctures with the petals.

*Calyx.*—comprises 4, very inconspicuous sepals of about 2 mm long and 1.5 mm wide, near (73) in color.

*Time of blooming.*—The plants flower year round in warm climates, with peak flowering occurring during warm summer months in tropical locations which have seasons.

*Duration of blooms.*—The individual flowers remain open for approximately 6 to 8 days before senescence.

Reproductive organs of the plant: Flowers are perfect.

*Pistils.*—Ovary is contained within the corolla tube and has a length of about 2 mm and comprises 2 locules; style is between about 2.5–3 cm 6 in length and 0.1 mm in diameter with a color of near (72). Stigma is bifurcated and the lobes are reflexed back to about the plane of the petals. Stigma is positioned just outside the tube and above the petals. Stigma is golden in color at anthesis. Stamens are 4 in number, inferior to the stigmas; one stamen is affixed to each petal at the juncture of the petal and the tube. Anthers are 2 mm long or less, and 1.5 mm in diameter with colors near (11 and 5). Seed production has not been observed on this plant; the fecundity has not been determined.

I claim:

1. A new and distinct variety of Ixora plant, as illustrated and described, particularly distinguished by its precocity, large, crowded corymbs of large diameter and high flower count, which contrast with its dark green, uniform leaves.

* * * * *